United States Patent
Kramer et al.

(10) Patent No.: US 10,945,613 B2
(45) Date of Patent: Mar. 16, 2021

(54) DETERMINING ARTERIAL WALL PROPERTY WITH BLOOD FLOW MODEL

(71) Applicants: Martin Kramer, Erlangen (DE); Lucian Mihai Itu, Brasov (RO); Viorel Mihalef, North Brunswick, NJ (US); Puneet Sharma, Monmouth Junction, NJ (US)

(72) Inventors: Martin Kramer, Erlangen (DE); Lucian Mihai Itu, Brasov (RO); Viorel Mihalef, North Brunswick, NJ (US); Puneet Sharma, Monmouth Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 852 days.

(21) Appl. No.: 15/479,465

(22) Filed: Apr. 5, 2017

(65) Prior Publication Data

US 2017/0281018 A1 Oct. 5, 2017

(30) Foreign Application Priority Data

Apr. 5, 2016 (EP) .................................... 16464005

(51) Int. Cl.
*A61B 5/02* (2006.01)
*A61B 5/026* (2006.01)
(Continued)

(52) U.S. Cl.
CPC .......... *A61B 5/02007* (2013.01); *A61B 5/026* (2013.01); *A61B 5/7278* (2013.01);
(Continued)

(58) Field of Classification Search
CPC ... A61B 5/02007; A61B 5/026; A61B 5/7278; A61B 6/507; A61B 8/06; A61B 6/504;
(Continued)

(56) References Cited

U.S. PATENT DOCUMENTS

| 2010/0016721 A1* | 1/2010 | Kanai ................. G01S 7/52042 600/443 |
| 2011/0060576 A1 | 3/2011 | Sharma et al. |

(Continued)

FOREIGN PATENT DOCUMENTS

EP 2942006 A1 11/2015

OTHER PUBLICATIONS

Elasticity imaging of atheroma with transcutaneous ultrasound both in longitudinal-axis and short-axis planes (Year: 2004).*

(Continued)

*Primary Examiner* — Hien N Nguyen
(74) *Attorney, Agent, or Firm* — Lempia Summerfield Katz LLC

(57) ABSTRACT

An estimation of arterial wall properties is provided. A method for determining a wall property of an artery such as an aorta includes acquiring patient data and extracting physical data from the patient data. The physical data is applied to a blood flow model of the aorta to obtain an individual blood flow model. The wall property of the artery is directly or indirectly determined from the individual blood flow model.

14 Claims, 3 Drawing Sheets

(51) Int. Cl.
| | |
|---|---|
| A61B 5/00 | (2006.01) |
| G16H 50/50 | (2018.01) |
| A61B 6/00 | (2006.01) |
| A61B 8/06 | (2006.01) |
| A61B 8/08 | (2006.01) |
| A61B 5/022 | (2006.01) |
| A61B 5/055 | (2006.01) |

(52) U.S. Cl.
CPC .............. *G16H 50/50* (2018.01); *A61B 5/022* (2013.01); *A61B 5/055* (2013.01); *A61B 6/504* (2013.01); *A61B 6/507* (2013.01); *A61B 8/06* (2013.01); *A61B 8/488* (2013.01)

(58) Field of Classification Search
CPC ......... A61B 8/488; A61B 5/022; A61B 5/055; G16H 50/50
See application file for complete search history.

(56) References Cited

U.S. PATENT DOCUMENTS

| | | |
|---|---|---|
| 2015/0038860 A1 | 2/2015 | Fonte et al. |
| 2015/0242589 A1 | 8/2015 | Neumann et al. |
| 2016/0029901 A1 | 2/2016 | Kuri |

OTHER PUBLICATIONS

Avolio, A. P., et al. "Effects of aging on changing arterial compliance and left ventricular load in a northern Chinese urban community." Circulation 68.1, pp. 50-58, (1983).

Brinton, T.J. et al.: "Arterial Compliance by Cuff Sphygmomanometer—Application to Hypertension and Early Changes in Subjects at Genetic Risk", in: Hypertension, vol. 28, pp. 599-603, (1996).

Chantler, P.D. et. al.: "Arterial-ventricular coupling: mechanistic insights into cardiovascular performance at rest and during exercise", in: J Appl Physiol 105: pp. 1342-1351, (2008).

European Search Report for European Application No. 16464005, dated Oct. 10, 2016.

Feng, J., and A. W. Khir. "Determination of wave speed and wave separation in the arteries using diameter and velocity." Journal of biomechanics 43.3, pp. 455-462 (2010).

Ibrahim, El-Sayed H., et al. "Measuring aortic pulse wave velocity using high-field cardiovascular magnetic resonance: comparison of techniques." Journal of Cardiovascular Magnetic Resonance 12.1, pp. 26-38 (2010).

Itu, Lucian, et al. "A parameter estimation framework for patient-specific hemodynamic computations." Journal of Computational Physics 28, pp. 316-333 (Oct. 22, 2014).

Itu, Lucian, et al. "A patient-specific reduced-order model for coronary circulation." Biomedical Imaging (ISBI), 2012 9th IEEE International Symposium on. IEEE, 2012.

Itu, Lucian, et al. "Non-invasive hemodynamic assessment of aortic coarctation: validation with in vivo measurements." Annals of biomedical engineering 41.4, pp. 669-681 (2013).

Khir, A.W. et. al.: "Determination of wave speed and wave separation in the arteries", in: Journal of Biomechanics, vol. 34, pp. 1145-1155, (2001).

Laurent, S. et. al.: "Expert consensus document on arterial stiffness: methodological issues and clinical applications", in: European Heart Journal, vol. 27, pp. 2588-2605 (2006).

Learoyd, B. M. et. al.: "Alterations with Age in the Viscoelastic Properties of Human Arterial Walls", Circ Res, vol. 18, pp. 278-292; (1966).

Low, K., et al. "An improved baseline model for a human arterial network to study the impact of aneurysms on pressure-flow waveforms." International journal for numerical methods in biomedical engineering 28.12, pp. 1224-1246 (2012).

Mitchel, G.F. et al. "Arterial stiffness and cardiovascular events: the Framingham Heart Study", in: Circulation 121, pp. 505-511, (2010).

Mynard J.P. et. al.: "A simple, versatile valve model for use in lumped parameter and one-dimensional cardiovascular models", in: Int. J. Numer. Meth. Biomed. Engng., vol. 28, pp. 626-641, (2012).

Nocedal, J. et. al.: "Numerical Optimization", Second Edition, Springer, New York, NY, USA, 2006.

Olufsen, Mette S., et al. "Numerical simulation and experimental validation of blood flow in arteries with structured-tree outflow conditions." Annals of biomedical engineering 28.11, pp. 1281-1299 (2000).

Raghu, R. et. al.: "Comparative Study of Viscoelastic Arterial Wall Models in Nonlinear One-Dimensional Finite Element Simulations of Blood Flow", in: Journal of Biomechanical Engineering, vol. 133 (Aug. 2011).

Reymond, Philippe, et al. "Validation of a patient-specific one-dimensional model of the systemic arterial tree." American Journal of Physiology-Heart and Circulatory Physiology 301.3, pp. H1173-H1182 (2011).

Saouti, N. et. al.: "Aortic function quantified: the heart's essential cushion", in: Journal of Applied Physiology, vol. 113, pp. 1285-1291 (2012).

Sipkema, Pieter, et al. "Isolated aorta setup for hemodynamic studies." Annals of biomedical engineering 185, pp. 491-503 (1990).

Steele et. al.: "Using One-Dimensional Finite Element, Analysis to Estimate Differential Pressure of Renal Artery Stenoses", in: Computers in Cardiology, vol. 34, pp. 391-394 (2007).

Stergiopulos, N., Patrick Segers, and N. Westerhof. "Use of pulse pressure method for estimating total arterial compliance in vivo." American Journal of Physiology-Heart and Circulatory Physiology 276.2, pp. H424-H428 (1999).

Vlachopoulos, C. et. al.: "Prediction of Cardiovascular Events and All-Cause Mortality With Arterial Stiffness", in: Journal of the American College of Cardiology, vol. 55, No. 13, pp. 1318-1327 (2010).

Vulliemoz S. et. al.: "Estimation of Local Aortic Elastic Properties With MRI", in: Magnetic Resonance in Medicine, vol. 47, pp. 649-654 (2002).

Westerhof, N. et. al. "Snapshots of hemodynamics: an aid for clinical research and graduate education." Springer Science & Business Media, 2010.

Westerhof, N. et. al.: "Analog studies of the human systemic arterial tree", in: J. Biomech., vol. 2, pp. 121-143, (1969).

Stergiopulos, N. M. J. W. N., J. J. Meister, and N. Westerhof. "Evaluation of methods for estimation of total arterial compliance." American Journal of Physiology-Heart and Circulatory Physiology 268.4 (1995): H1540-H1548.

Simon, A. Ch, et al. "An evaluation of large arteries compliance in man." American Journal of Physiology-Heart and Circulatory Physiology 237.5 (1979): H550-H554.

McVeigh, Gary E., et al. "Reduced vascular compliance as a marker for essential hypertension." American journal of hypertension 4.3_Pt_1 (1991): 245-251.

* cited by examiner

US 10,945,613 B2

DETERMINING ARTERIAL WALL PROPERTY WITH BLOOD FLOW MODEL

This application claims the benefit of EP16464005.4, filed on Apr. 5, 2016, which is hereby incorporated by reference in its entirety.

BACKGROUND

The present embodiments relate to determining a wall property of an artery.

Arterial distensibility is an important factor for the development and assessment of cardiovascular diseases [Laurent et al., 2006], [Mitchell et al., 2010], [Vlachopoulos et al., 2010]. Typically, the arterial distensibility is described by the arterial compliance (or the arterial elastance, the inverse of the compliance), which is responsible for important functional aspects of the systemic circulation: larger blood flow rate in the coronary arteries during diastole, reduction of left ventricular afterload (e.g., during systole), continuous flow at the level of the capillaries, etc. Previous studies have shown that arterial compliance changes with age [Avolio et al., 1983] or hypertension [Brinton et al., 1996]. The vast majority of the systemic compliance is given by the aorta and the large arteries bifurcating from the aorta [Sipkema et al., 1990]. Distribution along the arteries is non-uniform [Vulliemoz et al., 2002], [Westerhof et al., 1969] and changes with age [Learoyd et al., 1966].

The arterial wall properties at a certain location in the systemic circulation may be described by the local compliance, typically defined as area compliance, $C_A$, or by the local pulse wave velocity c. The arterial wall properties may also be described globally, for a certain region or for the entire systemic circulation, by the volume compliance $C_V$.

Several methods have been proposed in the past for non-invasive estimation of arterial wall properties [Westerhof et al., 2010]. Each of these methods has inherent limitations and difficulties when being applied in clinical practice. For example, the methods that rely on the transit time of the flow/pressure wave (e.g., the transit time is the time required for a flow/pressure wave to travel the distance between two locations) have a low accuracy if the distance used for the estimation of the transit time is relatively short. These methods may only provide an average value of the arterial wall properties for the region of interest.

In contrast, methods that estimate the local properties of the arterial wall are very sensitive to measurement noise: the ACM method [Saouti et al., 2012] estimates the local area compliance as $C_A=\Delta A/\Delta P$, where $\Delta A$ is the difference between minimum and maximum cross-sectional area during a heart cycle, and $\Delta P$ is the pulse pressure; the pulse pressure method (PPM) estimates the downstream volume compliance from the flow rate waveform and from the pulse pressure; —the PU-loop method [Khir et al., 2001] estimates the local wave speed as $c=dP/\rho dU$ during early systole, where dP is the derivative of the pressure and dU is the derivative of the blood flow velocity; the DU-loop method [Feng at al., 2010] estimates the local wave speed as $c=0.5\ dU/d(\ln D)$ during early systole, where dU is defined as above and D is the diameter.

SUMMARY AND DESCRIPTION

The scope of the present invention is defined solely by the appended claims and is not affected to any degree by the statements within this summary.

The methods described with reference to the prior art require accurate measurements/estimation of the pressure/velocity/area waveforms, which are not readily available or are susceptible to estimation errors when determined non-invasively.

The present embodiments may obviate one or more of the drawbacks or limitations in the related art. For example, a method for determining a wall property of an artery in a non-invasive way is provided.

According to one or more of the present embodiments, a method for determining a wall property of an artery (e.g., an aorta) includes acquiring patient data and extracting physical data from the patient data. The method also includes applying the physical data to a blood flow model of the artery to obtain an individual blood flow model and determining the wall property of the artery directly or indirectly from the individual blood flow model.

A device for determining a wall property of an artery (e.g., an aorta) is also provided. The device includes an acquiring device for acquiring patient data and a calculating device (e.g., a processor) for extracting physical data from the patient data. The calculating device is capable of applying the physical data to a blood flow model of the artery to obtain an individual blood flow model, and determining the wall property of the artery directly or indirectly from the individual blood flow model.

One or more of the present embodiments enable a robust and fully automatic method for patient-specific evaluation of the arterial function and of the local and regional arterial wall properties. The method may be based on a fluid structure interaction blood flow model that is personalized so as to closely match patient-specific quantities, which are extracted either through non-invasive measurements, or from medical images of the patient. Several pre-processing steps may extract the input information used for the blood flow computation, and, then, a comprehensive parameter estimation framework may be employed so as to personalize the boundary conditions and the wall properties in the regions of interest. As a result, both blood flow properties, like time-varying pressure and flow rate, and quantities describing the local and regional wall properties, like local wave speed, local area compliance, and downstream volume compliance, may be determined. The computed quantities of interest may be used in patient stratification, disease estimation, and/or therapy planning.

In one embodiment, the physical data includes an anatomical model of the artery and/or blood flow data. Such anatomical model may include geometrical dimensions of the aorta. Additionally or alternatively, the physical data may include blood flow data like velocity or blood pressure.

The blood flow model may be a fluid-structure interaction blood flow model. This provides that the model describes the interaction between the blood and the walls of the artery.

Additionally, the blood flow model may be based on a mass conservation equation and a longitudinal momentum conservation equation, both equations relying on a time-varying cross-sectional area and a time-varying flow-rate. Both equations are coupled by a state equation. Thus, a compact and physically accurate model is available.

In a further development, the method may include visualizing the wall property on an image of the artery (e.g., the aorta). The wall property is varying spatially with geometric coordinates. The advantage of the visualization is that the physician may easily estimate the condition of the artery.

In another embodiment, a local area compliance is directly determined as the wall property from the blood flow model. Such local area compliance helps to estimate local conditions of the artery.

A local wave speed of the blood in the artery may be determined from the blood flow model, and the wall property may be estimated from the local wave speed. This provides that the wall property of the artery may be indirectly estimated from the blood flow model via a local wave speed.

The method acts described in connection with the method may also be considered as functional features of the device.

DETAILED DESCRIPTION

The embodiments described below represent execution examples.

To overcome the limitations of the previously used computational approaches, an exemplary framework that is able to automatically and robustly estimate both local and regional wall properties from medical image data is provided. This framework may be based on a fluid-structure interaction (FSI) blood flow model, and on personalization procedures that estimate the parameters of the model so as to provide that the computational results match the patient-specific measurements. Under the exemplary method, patient data (e.g., medical images, non-invasive measurements, etc.) is acquired. Patient data (e.g., anatomical model, flow data, etc.) is extracted. Parameter estimation framework is applied based on a fluid-structure interaction blood flow model to robustly determine local and regional arterial wall properties. The computed data is visualized as outcome curves or as scalar and/or vector fields overlaid or displayed as attributes of the segmented geometries or the imaging data.

Any type of FSI blood flow model may be used. For example, a multiscale, three-dimensional, one-dimensional, lumped, or another type of FSI blood flow model may be used. Any type of medical imaging technique may be used to extract the input information required for the proposed framework. For example, magnetic resonance, ultrasound, Doppler, computer tomography, angiography, phase-contrast MR, or another type of medical imaging technique may be used to extract the input information.

Figure 1:
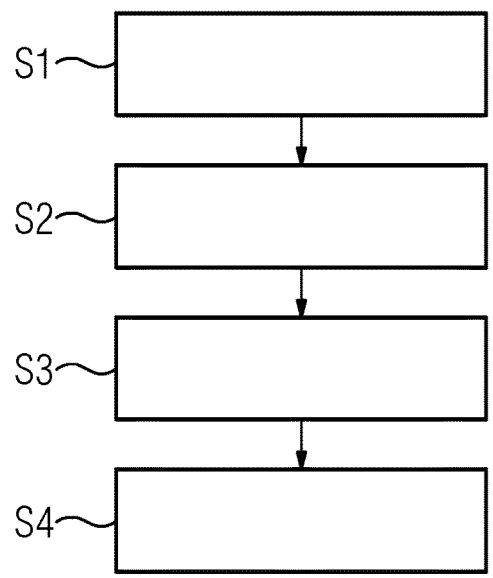
FIG. 1 shows a flow chart of one embodiment of a method.

FIG. 1 displays a flowchart of an embodiment of a method.

In act S1, patient data such as, for example, medical imaging data, non-invasive pressure, heart rate measurements, etc. is acquired. In a subsequent act S2, the patient data is pre-processed. Specifically, input data used for the estimation of the aorta wall properties (e.g., anatomical model, flow data, etc.) are extracted (e.g., in the following, the aorta is used representatively for any artery). Afterwards, in act S3, a parameter estimation framework based on, for example, fluid-structure interaction blood flow model may be applied to determine local and regional arterial wall properties. At act S4, the computed measures may be visualized.

In the following, acts S2 and S3 are focussed on, and details for specific embodiments are provided.

Since most of the systemic arterial compliance resides in the aorta, in the following, this part of the arterial circulation is focussed on. The methods described in the following, however, may also be applied to other large arteries.

As a result of processing act S2, the following information is available at a large number of planes (e.g., 50) along the ascending aorta, the aortic arch, and the descending aorta: time-varying cross-sectional area; time-varying flow rate; and time-varying center point.

Pressure information may be extracted from cuff-based non-invasive measurements performed at the left/right arm, and/or at the left/right leg.

Figure 2:
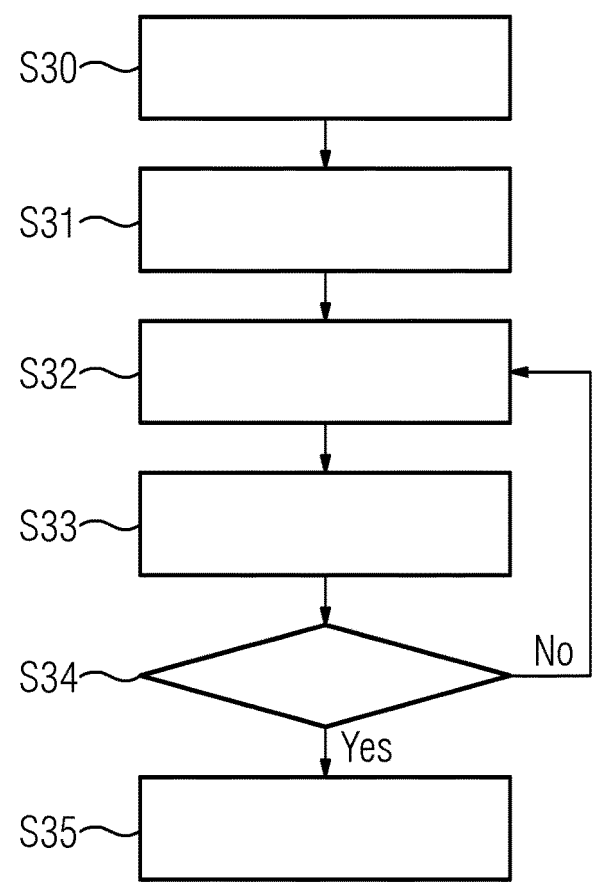
FIG. 2 shows a flow chart of an example of a parameter estimation framework for determining local and regional wall properties.

FIG. 2 displays an exemplary parameter estimation framework for determining the local and regional arterial wall properties according to act S3. In the following, an embodiment where a multiscale reduced-order blood flow model is employed is specifically referred to, but other full-scale or lumped parameter blood flow models may also be employed.

In act S30, anatomical and flow data are pre-processed. In act S31, a reduced-order blood flow model, for example, is initialized. According to act S32, a parameter estimation procedure is applied for determining outlet boundary conditions of the blood flow model. After act S32, a parameter estimation procedure for determining arterial wall properties is applied in act S33. In the following act S34, it is judged whether convergence criteria for estimation of outlet boundary conditions are met. If not, the method returns to act S32. If the convergence criteria of act S34 are met, the procedure jumps to act S35 for post-processing.

The reduced-order multiscale model is based on the one-dimensional formulation for the aorta (e.g., along the aortic centerline; compare FIG. 3) or the large arteries, for which anatomical information was extracted in the previous act, and, for example, on the three-element windkessel model for the downstream vasculature [Itu et al., 2013].

The one-dimensional blood flow model may be based on the mass conservation equation (1) and the longitudinal momentum conservation equation (2), which are coupled with a state equation (3) in order to close the system [Olufsen et al., 2000];

$$\frac{\partial A(x,t)}{\partial t} + \frac{\partial q(x,t)}{\partial x} = 0, \tag{1}$$

$$\frac{\partial q(x,t)}{\partial t} + \frac{\partial}{\partial t}\left(\alpha \frac{q^2(x,t)}{A(x,t)}\right) + \frac{A(x,t)}{\rho}\frac{\partial p(x,t)}{\partial x} = K_R \frac{q(x,t)}{A(x,t)}, \tag{2}$$

$$p(x,t) = \frac{4}{3}\frac{Eh}{r_0}\left(1 - \sqrt{\frac{A_0}{A(x,t)}}\right) + p_0, \tag{3}$$

where $A(x,t)$ is the time-varying cross-sectional area, $q(x,t)$ is the time-varying flow-rate, $p(x,t)$ is the time-varying pressure, $A_0$ is the initial cross-sectional area corresponding to the initial pressure $p_0$, E is the Young's modulus, h is the wall thickness and $r_0$ is the initial radius, $\alpha$ is the momentum-flux correction coefficient, $\rho$ is the density of the blood, and $K_R$ is a friction parameter corresponding to the viscous losses.

One-dimensional models have been shown to accurately predict time-varying flow rate and pressure wave forms under patient-specific conditions [Reymond et al., 2010]. Further, recent research activities have shown the growing interest in the one-dimensional blood flow model not only for the computation of a full body arterial model, but also for specific parts of the circulation in patient-specific pathologic situations: the coronary circulation [Itu et al., 2012], the abdominal aorta [Raghu et al., 2011], [Low et al., 2012], proximal part of the aorta [Itu et al., 2013], and the aortic valve [Mynard et al., 2012].

Figure 3:
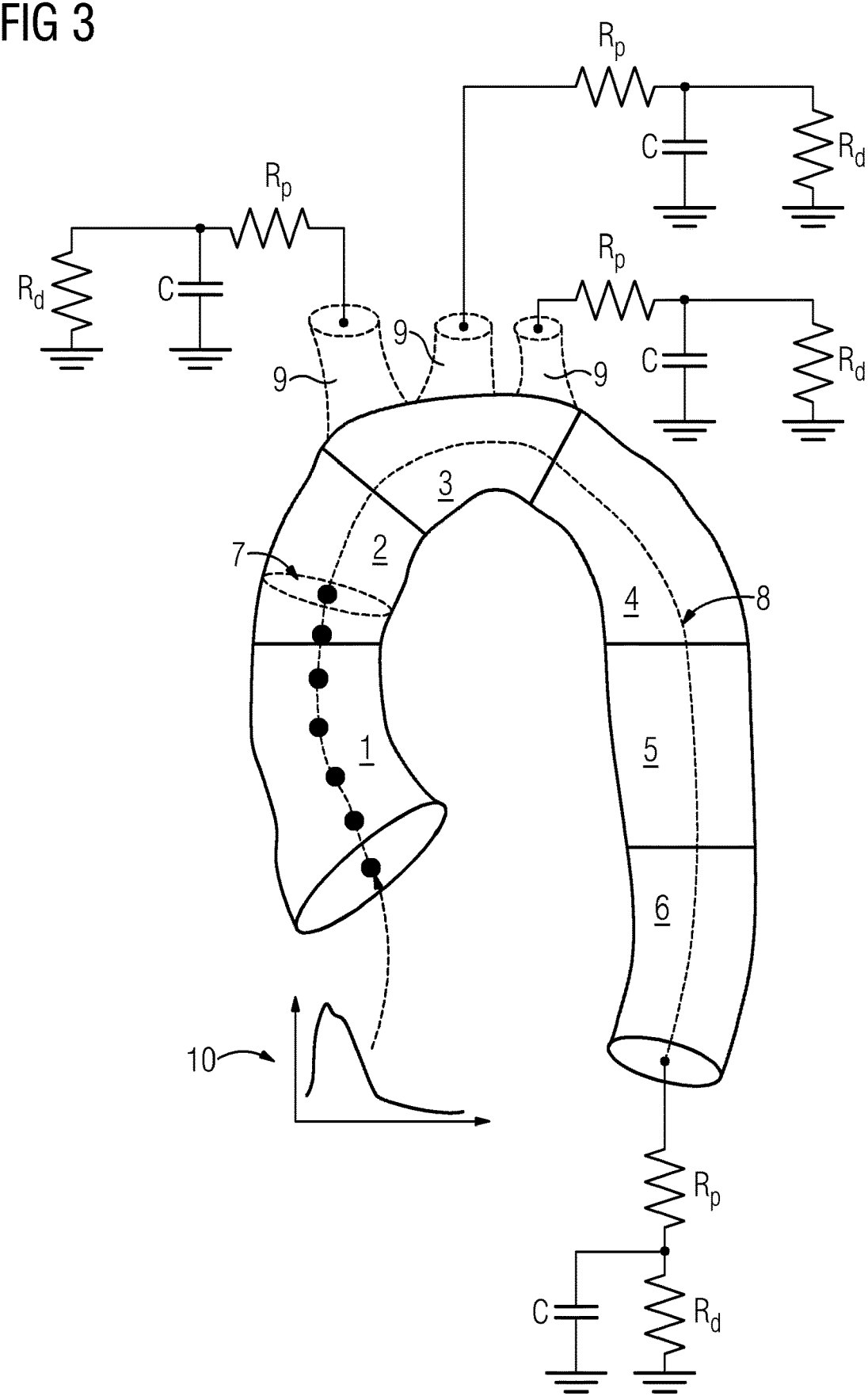
FIG. 3 shows an exemplary multiscale blood flow model.

FIG. 3 displays an exemplary multiscale blood flow model for the aorta and the supra-aortic branches. The aorta is divided into a number of segments for which blood is then computed based on the model described above. Six different segments 1 to 6 are displayed in FIG. 3, but this number may be higher or lower depending on the actual length of the aorta. Roughly, the segments 1 and 2 correspond to the ascending aorta. The segments 2, 3 and 4 describe the aortic arch. The segments 4 to 6 may be assigned to the descending aorta. A cross-section of the aorta may represent a plane 7 for which A(t) and Q(t) are provided. A centerline 8 runs in the middle of the aorta. Supra-aortic branches 9 are typically positioned at the top of the aortic arch. The outputs of the aorta as well as the supra-aortic branches 9 may be represented by an electrical equivalent circuit including a resistance $R_p$ in series with a parallel circuit of a capacitance C and a resistance $R_d$.

At the inlet of the aorta, a time-varying flow rate profile 10 may be imposed as inlet boundary condition, while the parameters of the outlet windkessel boundary conditions are set as described below.

Figure 4:
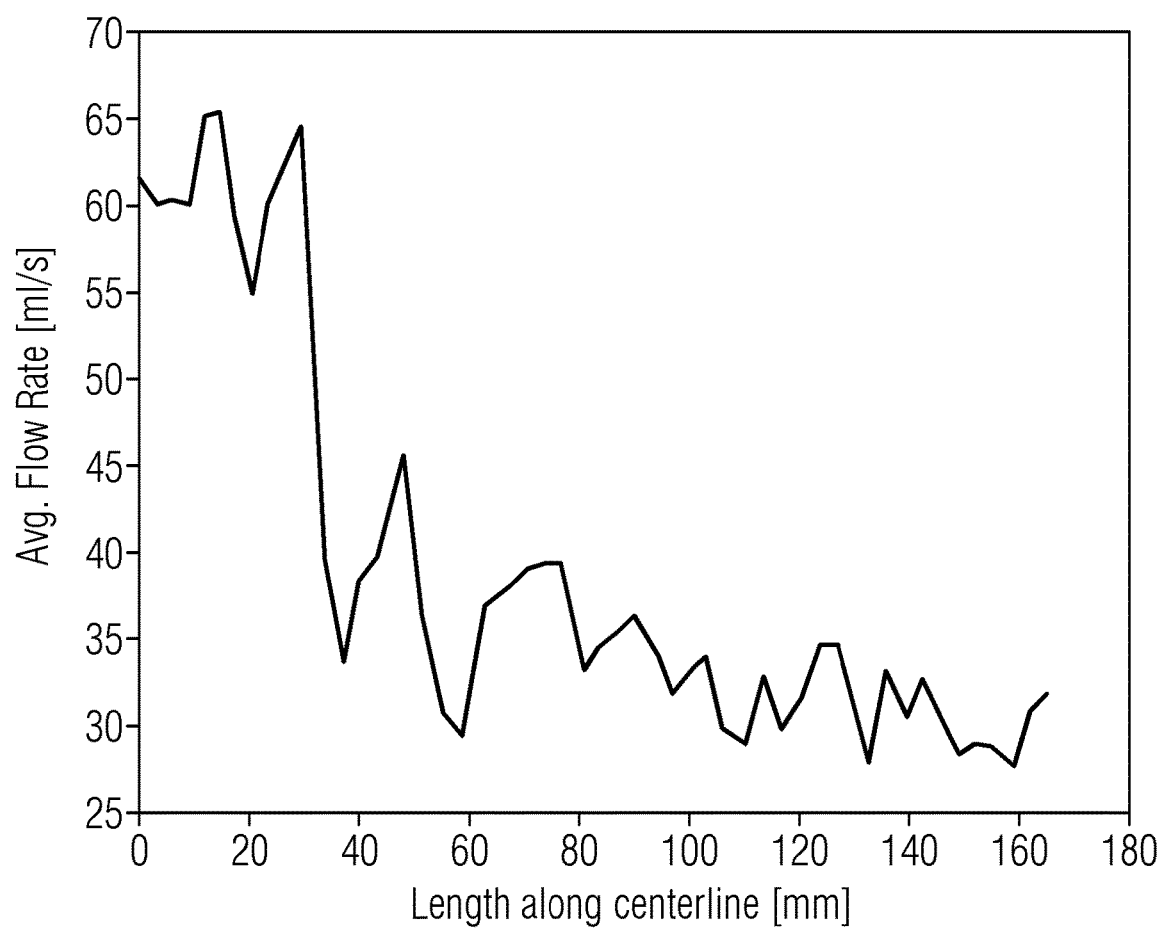
FIG. 4 shows an exemplary average flow rate determined along the centerline of the aorta.

Concerning act 31 for pre-processing anatomical and flow data, anatomical and flow rate information is only available for the aorta or another specific artery. However, to be able to run a reliable blood flow computation for, for example, the aorta, supra-aortic branches are to be provided. These draw away from the aorta a certain volume of blood. If supra-aortic branches are not added to the geometric model, the descending aorta would have the same average flow rate as the ascending aorta and as a result considerable errors would be expected in the estimation of the arterial wall properties (e.g., typically the flow rate in the descending aorta is 30-50% lower than in the ascending aorta). FIG. 4 displays an example of how the average flow rate, as determined from 4D flow data, varies along the centerline of the aorta. A gradual decrease in flow rate may be observed between a length of 30 and 70 mm along the centerline.

To determine the bifurcation point of the first supra-aortic branch (e.g., the brachiocephalic artery), an algorithm that, starting from the ascending aorta inlet, navigates through the centerline locations until the average flow rate at the current location decreases below a threshold value given by the average flow rate of the previous centerline locations, is employed.

Similarly, to determine the bifurcation point of the third supra-aortic branch (e.g., the left subclavian artery), an algorithm that, starting from the descending aorta outlet, navigates in reverse direction through the centerline locations until the average flow rate at the current location increases above a threshold value given by the average flow rate of the downstream centerline locations, is employed.

The bifurcation point of the second supra-aortic branch (e.g., the left common carotid artery) is set midway between the other two supra-aortic branches.

As shown in FIG. 4, due to measurement noise, the average flow rate in the ascending and the descending aorta varies slightly from one location to the next. To robustly estimate an average flow rate value for the ascending and the descending aorta, a linear least squares fit based algorithm that is used to filter out locations with very large or very low average flow rate values is employed. Then, based on the remaining locations, a final average flow rate value is determined for the ascending and the descending aorta.

The initialization of the reduced-order blood flow model according to act S31 includes: a) defining the 1D segments and corresponding geometry; b) defining the inlet boundary condition and the initial parameter values at the outlet boundary condition; and c) defining the initial arterial wall properties.

At act (a), the number of segments is defined for each branch. Typically, a single segment is used for the aortic arc branches. Multiple 1D segments with spatially varying cross-sectional area values are defined for the ascending and descending aorta in order to obtain a geometry close to the actual 3D geometry. The initial pressure and cross-sectional area values are based on the end-diastolic phase.

For the supra-aortic branches, population-average geometric properties [Reymond et al., 2010] may be used, and a constant length of 2 cm may be set for each of these branches.

At act (b), the inlet boundary condition is defined. The flow rate profile at the first analysis plane is scaled so as to match the average ascending aorta flow rate value estimated, as described in the previous section. Three initial parameter values are to be specified at each outlet. The average pressure at the start of the left subclavian artery is computed following an approach described in [Saouti et al., 2012]. The brachial systolic pressure $P_{b-s}$ and the brachial diastolic pressure $P_{b-d}$ are used as input. The diastolic pressure at the start of the left subclavian artery is set equal to $P_{b-d}$, while the systolic pressure is computed using:

$$P_{LSA-s}=0.83P_{b-s}+0.15P_{b-d}. \qquad (4)$$

The mean arterial pressure at the start of the left subclavian artery is computed using a form factor of 0.4:

$$\overline{P}_{LSA}=0.4P_{LSA-s}+0.6P_{LSA-d}. \qquad (5)$$

Since the variation of the average arterial pressure in the aorta is small, $\overline{P}_{LSA}$ is used for computing the total resistance at each outlet as ratio between average pressure and average flow rate:

$$R_t=\overline{P}/\overline{Q}. \qquad (6)$$

To determine the average flow rate at each supra-aortic branch, the total supra-aortic average flow rate $Q_{supra-aortic}$ is computed as a difference between the average flow rates in the ascending and the descending aorta. This flow is then distributed to the branching vessels proportionally to the square of the radius [Steele at al., 2007]. Thus, $$Q_i = Q_{supra-aortic} \cdot r_i^2 / \sum_{i=1}^{3} r_i^2, \qquad (7)$$

where $r_i$ is the radius of the supra-aortic branch i.

The proximal resistance of each windkessel model is set equal to the characteristic resistance of the corresponding outlet segment, while the distal resistance is computed as difference between total and proximal resistance.

For the estimation of compliance values, a population average compliance value ($C_{tot}$) [Low et al., 2012] that is then distributed to the four outlets as follows is first considered:

$$(C)_i = \frac{c_{tot} \cdot r_i^2}{\sum_{i=1}^{3} r_i^2}. \tag{8}$$

At act (c), the arterial wall properties are determined at the bifurcation of the left subclavian artery. Eq. (3) is rewritten, based on $P_{LSA-s}$ and $P_{LSA-d}$ as:

$$P_{LSA-s} = \beta\left(1 - \sqrt{\frac{A_{LSA-d}}{A_{LSA-s}}}\right) + P_{LSA-d}, \tag{9}$$

where $A_{LSA-s}$ and $A_{LSA-d}$ are the maximum (systolic) and minimum (diastolic) cross-sectional area values determined as described in section 3.2 and $\beta$ represents the wall stiffness. Hence:

$$\beta = \frac{4}{3}\frac{Eh}{r_0} = (P_{LSA-s} - P_{LSA-d})/\left(1 - \sqrt{\frac{A_{LSA-d}}{A_{LSA-s}}}\right). \tag{10}$$

This stiffness value is then used as an initial value for the entire aorta. To estimate the wall properties of the supra-aortic vessels, a slightly modified approach, under which the wall properties of each supra-aortic segment are computed separately, is used. This is done to minimize the wave reflections at the bifurcations. Under this approach, first the reflection coefficient at a bifurcation is computed [Reymond et al., 2010]:

$$\Gamma = \frac{Y_p - \sum_i (Y_d)_i}{Y_p + \sum_i (Y_d)_i}. \tag{11}$$

where $Y_p$ ($Y_d$) is the characteristic admittance of the parent (daughter) vessel. The characteristic admittance is the inverse of the characteristic resistance of a vessel. The characteristic resistance of each supra-aortic vessel is computed by setting $\Gamma$ equal to 0:

$$R_{supra-aortic} = R_{aorta-p} \cdot R_{aorta-d}/(R_{aorta-d} - R_{aorta-p}). \tag{12}$$

Once the characteristic resistance is known, $E \cdot h/r_0$, is determined as follows:

$$\frac{E \cdot h}{r_0} = \frac{3 \cdot Z_{supra-aortic} \cdot \pi^2 \cdot r_0^4}{2 \cdot \rho}. \tag{13}$$

The objective of act 32 (e.g., parameter estimation procedure for determining outlet boundary conditions) is to adapt, for example, the parameters of the windkessel models coupled to the outlets of the geometric model, under the constraint that the blood flow solutions should i) maintain the same flow-split at each outlet as with the measured data, and ii) replicate the measured systolic and diastolic pressure at the start of the left subclavian artery. Out of the four flow-split values, only three are used as objectives, since the fourth one is obtained automatically as a difference.

The parameter estimation problem is formulated as a solution to a system of nonlinear equations, with each equation representing the residual error between the computed and measured quantity of interest. To determine the values of all the residuals ($f(x_i)$), a computation with the parameter values is to be provided. Since the absolute values of the adapted parameters and of the residuals generally differ by orders of magnitude, for the calibration method both the parameter and the objective residuals have been scaled using typical values.

The parameters to be estimated are the total resistances of the three supra-aortic vessels and of the descending aorta, and the total compliance. The following system of nonlinear equations is numerically solved to obtain the optimum value of each parameter:

$$f\begin{pmatrix} R_{t-BC} \\ R_{t-LCC} \\ R_{t-LS} \\ R_{t-DAo} \\ C \end{pmatrix} = \begin{Bmatrix} (P_{max})_{comp} - (P_{max})_{ref} \\ (P_{min})_{comp} - (P_{min})_{ref} \\ (\Phi_{BC})_{comp} - (\Phi_{BC})_{ref} \\ (\Phi_{LCC})_{comp} - (\Phi_{LCC})_{ref} \\ (\Phi_{DAo})_{comp} - (\Phi_{DAo})_{ref} \end{Bmatrix} = \begin{pmatrix} 0 \\ 0 \\ 0 \\ 0 \\ 0 \end{pmatrix}, \tag{14}$$

where $P_{max}$ is the maximum (systolic) pressure, $P_{min}$ is the minimum (diastolic) pressure, both at the start of the left subclavian artery, ($\Phi$). represents a flow rate split, while $(\bullet)_{comp}$ refers to a value computed using the 0D/Multiscale model, and $(\bullet)_{ref}$ refers to the reference value. Index BC refers to the brachiocephalic artery, LCC to the left common carotid artery and $DA_O$ to the descending aorta.

The nonlinear system of equations is first solved for a 0D model, composed of the windkessel models used in the multiscale model. The initial solution $x_0$ is determined using the steps described in the previous section and then a dogleg trust region algorithm is applied to iteratively determine the solution of the nonlinear system of equations. The solution determined for the 0D model is then adapted as described in [Itu et al., 2015], and used as initial solution for the multiscale reduced-order blood flow model. A quasi-Newton method is employed at this stage, whereas the Jacobian is only updated and not recomputed at each iteration in order to provide short computation times. If all objective residuals are smaller than the tolerance limit (el), the calibration method is terminated.

The objective of this act S33 (e.g., parameter estimation procedure for determining arterial wall properties) is to adapt the local wall stiffness along the aorta so as to obtain a good match between the measured and the computed cross-sectional area variation at the analysis planes.

The parameter estimation procedure is based on a non-linear least squares method, which minimizes the following cost function:

$$f(x) = \frac{1}{2}\sum_{j=1}^{m} r_j^2(x), \tag{15}$$

where m is the total number of measurements, j refers to a specific measurement location along the aorta, and $r_j(x)$ are the residuals computed as difference between the measured and the computed quantities:

$$r_j(x) = \Delta A_j^{ref} - \Delta A_j^{comp}, \tag{16}$$

where $\Delta A_j^{ref}$ is the measured maximum variation in the cross-sectional area during a heart cycle at location j, and $\Delta A_j^{comp}$ is the computed maximum variation in the cross-sectional area during a heart cycle at location j.

The parameter vector x contains the wall stiffness at the start and end of each 1D segment in the computational model (e.g., a linearly varying stiffness is imposed between the start and the end of each 1D segment):

$$x = [\beta_{1\text{-}start}, \beta_{1\text{-}end}, \beta_{2\text{-}start}, \beta_{2\text{-}end} \cdots]^T, \quad (17)$$

The cost function is minimized based on a quasi Gauss-Newton method, which performs a line search in the direction $p_k^{GN}$ and chooses a step length $\alpha_k$ so as to satisfy the Armijo and Wolfe conditions [Nocedal et al., 2006]. Similar to the setup in the previous section, the Jacobian is only computed once and then updated at each further iteration. Once the cost function converges (e.g., variation from one iteration to the next becomes smaller than 1%), the calibration method is terminated.

Once the parameter estimation procedure for determining the arterial wall properties has converged, the convergence criteria (see equation 14) of the parameter estimation procedure for determining the outlet boundary conditions are verified (act S34). If these are not satisfied, the two parameter estimation procedures are run again. The convergence criteria of the first parameter estimation procedure may no longer be satisfied once the second parameter estimation procedure has been applied, since a change in the wall properties generally induces a change in the pressure and flow rate values.

During the post-processing act S35, several quantities of interest are computed from the computational results of the parameter estimation framework:

1. The local wave speed:

$$c(x) = \sqrt{\frac{\beta(x)}{2\rho}}, \quad (18)$$

where x refers to the length coordinate along the centerline of the aorta

2. The local area compliance from the local wall stiffness:

$$C_A(x) = \frac{2A(x)}{\beta(x)}, \quad (19)$$

where A(x) is the average value of the cross-sectional area at location x.

3. The local area compliance using the ACM method:

$$C_{A\text{-}ACM}(x) = \frac{\Delta A(x)}{PP(x)}, \quad (20)$$

where $\Delta A(x)$ is the maximum variation of the cross-sectional at location x, and PP(x) is the pulse pressure at location x.

4. The downstream volume compliance:

$$C_V(x) = PPM(q(x,t), PP(x)), \quad (21)$$

where PPM refers to the pulse pressure method, which uses as input the time-varying flow rate at location x and the pulse pressure at location x.

The following variations and extensions are possible:

1. If flow rate/cross-sectional area measurements are available for the supra-aortic branches, these may be used to enable a better estimation of the branching locations and/or the flow rate distribution.

2. The herein proposed framework may also be applied in various pathological cases, like coarctation cases with or without collateral vessels.

3. The herein proposed framework may also be used to estimate the elastance (inverse of the compliance) of the aorta that is typically used to evaluate the ventricular-arterial coupling [Chantler et al., 2008], as an important indicator of the function of the cardiovascular system.

4. If invasive pressure measurements are available (e.g., as provided by a catheterization procedure), these may be used to further improve the personalization of the hemodynamic model. For example, these may be used directly as objectives in the parameter estimation framework.

5. The herein proposed framework may be used to estimate the wall properties and associated quantities of interest in any part of the systemic circulation and the cardiovascular system.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a wall property of an artery, the method comprising:
    acquiring patient data, wherein acquiring the patient data includes medical imaging;
    extracting physical data from the patient data;
    obtaining an individual blood flow model, the obtaining comprising applying the physical data to a blood flow model of the artery;
    determining the wall property of the artery directly or indirectly from the individual blood flow model, the wall property comprising arterial compliance, arterial elastance, or arterial compliance and arterial elastance, wherein determining the wall property comprises adapting a wall stiffness along the artery, such that a measured cross-sectional area variation of the artery acquired from the medical imaging is matched with a computed cross-sectional area variation of the artery according to the individual blood flow model; and
    displaying the wall property on an image of the artery, such that a condition of the artery is estimable by a physician, wherein the wall property varies spatially with geometric coordinates on the image of the artery.

2. The method of claim 1, wherein acquiring the patient data includes a non-invasive measurement.

3. The method of claim 1, wherein the physical data includes an anatomical model of the artery, blood flow data, or the anatomical model of the artery and the blood flow data.

4. The method of claim 1, wherein the blood flow model is a fluid-structure interaction blood flow model.

5. The method of claim 1, wherein the blood flow model is based on a mass conservation equation and a longitudinal momentum conservation equation, the mass conservation equation and the longitudinal momentum conservation equation both relying on a time-varying cross-sectional area and a time-varying flow-rate, and wherein the mass conservation equation and the longitudinal momentum conservation equation are coupled by a state equation.

6. The method of claim 1, wherein determining the wall property of the artery comprises directly determining a local area compliance as the wall property from the blood flow model.

7. The method of claim 1, further comprising determining a local wave speed of blood in the artery from the blood flow model, wherein determining the wall property of the artery comprises estimating the wall property from the local wave speed.

8. The method of claim 1, wherein the artery is an aorta.

9. A device for determining a wall property of an artery, the device comprising:

an acquisition device configured to acquire patient data, wherein the acquisition device is a medical imaging device, and wherein acquisition of the patient data includes medical imaging; and a processor configured to:

extract physical data from the patient data;

obtain an individual blood flow model, the obtainment of the individual blood flow model comprising application of the physical data to a blood flow model of the artery;

determine the wall property of the artery directly or indirectly from the individual blood flow model, the wall property comprising arterial compliance, arterial elastance, or arterial compliance and arterial elastance, the determination of the wall property comprising adaptation of a wall stiffness along the artery, such that a measured cross-sectional area variation of the artery acquired from the medical imaging is matched with a computed cross-sectional area variation of the artery according to the individual blood flow model; and display the wall property on an image of the artery, such that a condition of the artery is estimable by a physician, wherein the wall property varies spatially with geometric coordinates on the image of the artery.

10. The device of claim 9, wherein the artery is an aorta.

11. The device of claim 9, wherein the acquisition of the patient data includes a non-invasive measurement.

12. The device of claim 9, wherein the physical data includes an anatomical model of the artery, blood flow data, or the anatomical model of the artery and the blood flow data.

13. The device of claim 9, wherein the blood flow model is a fluid-structure interaction blood flow model.

14. The device of claim 9, wherein the blood flow model is based on a mass conservation equation and a longitudinal momentum conservation equation, the mass conservation equation and the longitudinal momentum conservation equation both relying on a time-varying cross-sectional area and a time-varying flow-rate, and wherein the mass conservation equation and the longitudinal momentum conservation equation are coupled by a state equation.

* * * * *